United States Patent [19]

McGee

[11] Patent Number: 5,198,216

[45] Date of Patent: Mar. 30, 1993

[54] PERFORMANCE ENHANCING COMPOSITIONS OF MATTER, AND METHODS OF PREPARING AND UTILIZING SAME

[75] Inventor: David M. McGee, Grosse Pointe Park, Mich.

[73] Assignee: Daliff Corporation, Miami, Fla.

[21] Appl. No.: 559,661

[22] Filed: Jul. 30, 1990

[51] Int. Cl.$^5$ .................... A61K 37/62; A61K 35/78; A61K 35/42; A61K 35/23; A61K 35/48; A61K 35/55; A61K 35/34; A61K 35/28; A61K 33/24; A61K 33/14; A61K 33/06; A61K 33/08; A61K 31/70; A61K 31/495; A61K 31/50; A61K 31/51; A61K 31/44; A61K 31/34; A61K 31/195; A61K 31/14; A61K 31/07

[52] U.S. Cl. .................... 424/94.2; 424/195.1; 424/557; 424/558; 424/559; 424/563; 424/565; 424/568; 424/569; 424/570; 424/579; 424/580; 424/617; 424/681; 424/682; 424/692; 514/52; 514/249; 514/251; 514/276; 514/345; 514/355; 514/474; 514/562; 514/563; 514/642; 514/725

[58] Field of Search ............... 424/563, 565, 559, 580, 424/568, 579, 558, 570, 557, 569, 94.2, 195.1, 617, 681, 682, 692; 514/251-276, 355, 474, 562, 772, 904, 905, 52, 249, 345, 563, 642, 725

[56] References Cited

U.S. PATENT DOCUMENTS

| | | | |
|---|---|---|---|
| 1,753,531 | 4/1930 | Prince | 424/565 |
| 2,193,523 | 3/1940 | Schultz | 424/558 |
| 4,749,522 | 6/1988 | Kamarei | 424/565 |
| 4,908,206 | 3/1990 | Schäfer et al. | 424/558 |

FOREIGN PATENT DOCUMENTS 46-38591  11/1971  Japan.

OTHER PUBLICATIONS

The Merck Veterinary Manual, 3rd Edition, (1967), pp. 1415-1419 and 1441-1452.

*Primary Examiner*—Frederick E. Waddell
*Assistant Examiner*—Raymond J. Henley, III
*Attorney, Agent, or Firm*—Irving M. Weiner; Joseph P. Carrier; Pamela S. Burt

[57] ABSTRACT

A composition for enhancing the performance of animals, such as horses or dogs, is composed of adrenal and pituitary raw tissue concentrates, vitamin C, bioflavonoid complex, pantothenic acid, methionine, choline, vitamin B1, vitamin B2, vitamin B6, niacinamide, magnesium, vitamin B12, folic acid and organic iodine. The composition is adapted to be orally administered to an animal, is composed of all natural substances, and the relative proportions of the components are approximately:

at least 40 parts adrenal raw tissue concentrate to
at least 2 parts pituitary raw tissue concentrate to
30-60 parts vitamin C to
20-30 parts magnesium to
10-20 parts of each of pantothenic acid, methionine and choline to
8-15 parts of each of niacinamide and bioflavonoid complex to
1-5 parts of each of vitamins B1, B2 and B6 to
0.1-1 parts organic iodine to
0.05-0.5 parts folic acid.

Also, a method of biochemically enhancing an animal's performance is disclosed, comprising the steps of: (a) obtaining a sample of body fluid of an animal which is performing below expected levels, (b) analyzing the sample to determine a composition thereof, (c) comparing the determined composition of the fluid to predetermined appropriate parameters, (d) determining a performance enhancing composition to be administered to the animal based on the comparison and on additional predetermined data, (e) administering a predetermined dosage of the composition to the animal for a predetermined period of time, and (f) repeating steps (a)-(c) to determine if a desired change in the fluid composition of the animal has been achieved.

20 Claims, 1 Drawing Sheet

PERFORMANCE ENHANCING COMPOSITIONS OF MATTER, AND METHODS OF PREPARING AND UTILIZING SAME

BACKGROUND OF THE INVENTION

1. Field of the Invention

The present invention relates to novel compositions for use in enhancing the performance of animals, such as horses, which compositions are composed entirely of natural substances and are adapted to be orally administered to the animals. The invention also relates to methods of preparing and utilizing the aforementioned compositions.

2. Description of Relevant Art

There are known methods and compositions for enhancing the performance of animals such as horses, dogs, etc. For example, in the field of horse racing it is known that a horse's performance can be significantly affected by injecting the horse with a quantity of adrenalin prior to a race. Such use of adrenalin is, however, substantially regulated or prohibited by law. Furthermore, such use of adrenalin is often disadvantageous because the chemical's performance-enhancing effect on a horse is generally quickly achieved and short-lived. Thus, if a horse is injected with adrenalin prior to a race while waiting in its stall (prior to being called to the gate) it is very possible that the adrenalin's performance-enhancing effect on the horse will occur while the animal remains in the stall, or before the race has even begun.

The present invention has been developed to overcome the disadvantages of known compositions and methods for enhancing the performance of animals such as horses, dogs, etc.

SUMMARY OF THE INVENTION

According to the present invention there is provided a composition for enhancing the performance of animals, such as horses or dogs, which is composed of adrenal and pituary raw tissue concentrates, vitamin C, bioflavonoid complex, pantothenic acid, methionine, choline, vitamin B1, vitamin B2, vitamin B6, niacinamide, magnesium, vitamin B12, folic acid and organic iodine. The composition is adapted to be orally administered to an animal, is composed of all natural substances, and the relative proportions of the components are approximately:

- at least 40 parts adrenal raw tissue concentrate to
- at least 2 parts pituitary raw tissue concentrate to
- 30-60 parts vitamin C to
- 20-30 parts magnesium to
- 10-20 parts of each of pantothenic acid, methionine and choline to
- 8-15 parts of each of niacinamide and bioflavonoid complex to
- 1-5 parts of each of vitamins B1, B2 and B6 to
- 0.1-1 parts organic iodine to
- 0.05-0.5 parts folic acid.

Also, a method of biochemically enhancing an animal's performance is disclosed, comprising the steps of: (a) obtaining a sample of body fluid of an animal which is performing below expected levels, (b) analyzing the sample to determine a composition thereof, (c) comparing the determined composition of the fluid to predetermined appropriate parameters, (d) determining a performance enhancing composition to be administered to the animal based on the comparison and on additional predetermined data, (e) administering a predetermined dosage of the composition to the animal for a predetermined period of time, and (f) repeating steps (a)-(c) to determine if a desired change in the fluid composition of the animal has been achieved.

It is an object of the present invention to provide compositions for enhancing the performance of animals, which compositions are composed entirely of natural substances and are adapted to be orally administered to the animals.

It is another object of the present invention to provide such compositions which can be easily administered to an animal in relation to the performance of a given event.

It is another object of the present invention to provide such compositions which are specifically formulated for use by a given animal, and which are adapted to be administered to the animal for an extended period of time for generally improving the animal's performance.

Still another object of the present invention is to provide a method of biochemically enhancing an animal's performance by specially formulating a composition tailored to predetermined needs to the animal, and administering the composition to the animal for a predetermined time period.

Other objects and details of the invention will become apparent from the following detailed description of the invention.

DETAILED DESCRIPTION OF PREFERRED EMBODIMENTS

Figure 1:
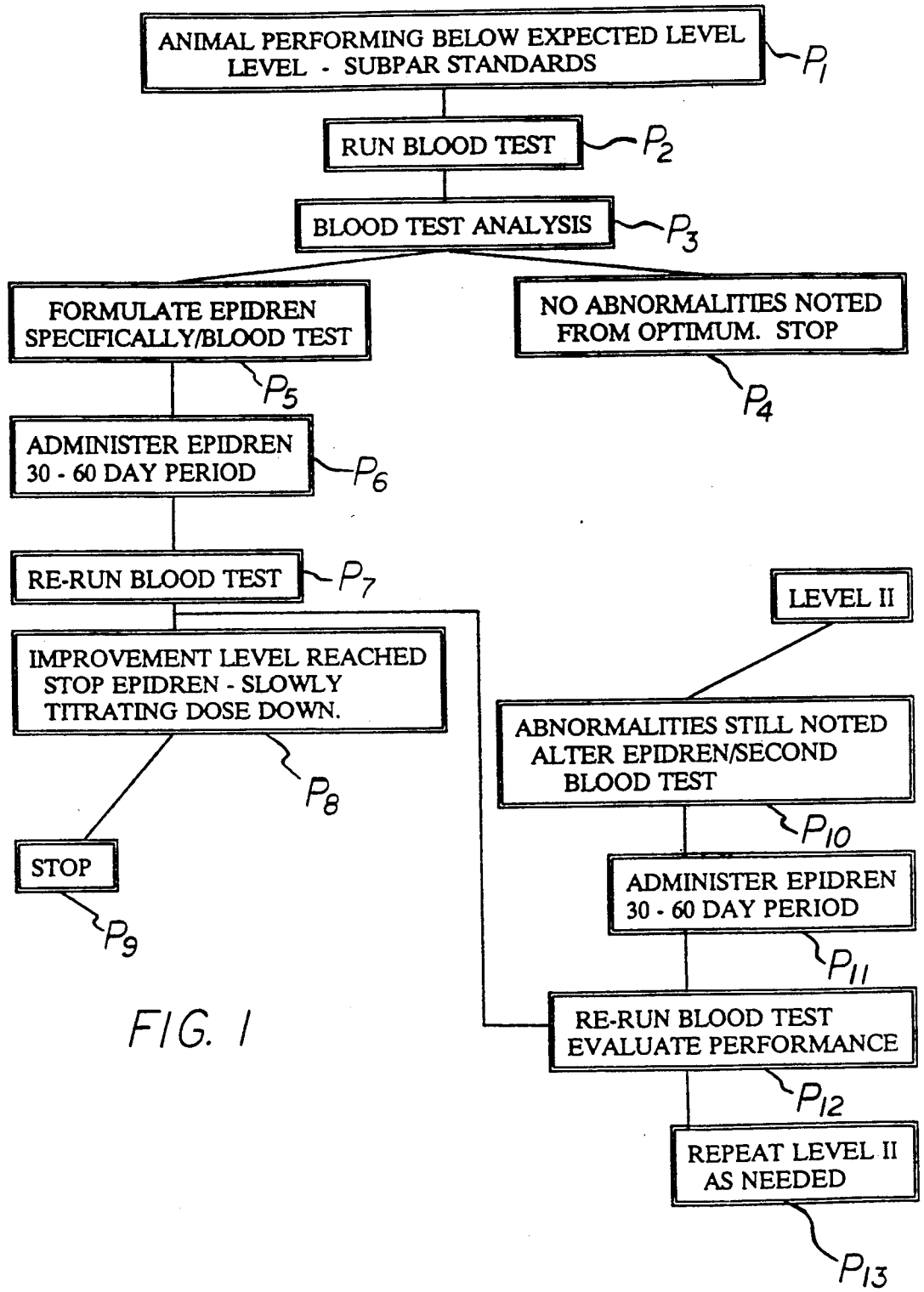
FIG. 1 is a flow chart of a method according to the present invention.

Referring to FIG. 1, there is shown a method in accordance with the present invention for generally improving an animal's performance. Step $P_1$ is simply recognizing that an animal is performing below expected levels, and would be recognized by the animal's owner and/or trainer. It will be understood that this step is not part of the present invention, but merely a preliminary act identifying a need for the present invention. At step $P_2$ a sample of the animal's blood or other body fluid is obtained, while at step $P_3$ the fluid sample is analyzed to determine a composition thereof, which determined composition is then compared to predetermined appropriate compositional parameters. The appropriate compositional parameters are experimentally predetermined relative to the type of animal in question, i.e., horse, dog, etc, the animal's weight, etc. If it is determined through such comparison that the animal's blood composition falls within the predetermined appropriate parameters, then the method ends at step $P_4$.

On the other hand, if the determined composition does not fall within the predetermined appropriate parameters, then a performance enhancing composition to be administered to the animal is determined at step $P_5$ based on the results of the comparison and on additional predetermined data. Such additional predetermined data would include information on increasing and/or decreasing each of the compositional parameters, or combinations of the parameters, analyzed in the animal's fluid sample. At step $P_6$ a predetermined dosage of the formulated composition, generally based on the animal's weight, is administered to the animal for a predetermined time period. Preferably such time period is approximately 30–60 days. Also, it is preferred that the composition will be orally administered to the animal twice daily. For example, the composition could be orally administered to the animal in liquid form by pouring or otherwise forcing a solution of the composition directly down the animal's throat, or a powder form of the composition could be added to the animal's food. It is most preferred that the composition will be administered to the animal prior to feeding.

After the composition has been administered to the animal for the predetermined time period, another sample of the animal's blood is obtained and analyzed at step $P_7$. If the analysis indicates that a desired change or improvement in the animal's blood has been achieved in comparison to the original blood sample, then a progressively smaller (or diluted) quantity of the composition is administered to the animal for a another predetermined time period at step $P_8$, and the treatment for the given animal is ended at step $P_9$.

If the analysis performed at step $P_7$ indicates that a desired change in the composition of the animal's fluid has not been achieved relative to the initial fluid sample analysis, then a different performance enhancing composition to be administered to the animal is determined at step $P_{10}$. The different composition is administered to the animal for another predetermined time period at step $P_{11}$, after which another sample of the animal's blood is obtained and analyzed at step $P_{12}$ to determine if desired change in the fluid's composition has been achieved. If a desired change has been achieved the method is ended through steps $P_8$, $P_9$, and if a desired change in the fluid's composition has not been achieved level II (including steps $P_{10}+$) is repeated until a desired change in the fluid composition is achieved, as indicated at $P_{13}$.

The fluid (blood) analyses performed at steps $P_3$, $P_7$, and $P_{12}$ will determine at least a chemical composition of the analyzed fluid. If the fluid is blood, then the analysis will preferably also determine hematological and differential compositions of the blood, as well as the chemical composition of the blood.

The performance enhancing compositions determined at steps $P_5$ and $P_{10}$ will include one or more of the following components in varying amounts depending on the change desired to be effected in the animal's fluid (blood) composition and on other factors such as the type and weight of the specific animal involved: raw tissue concentrates of adrenal, pituitary, thyroid, orchic protomorphogen, thymus, spleen, kidney, hypothalamus, pulmonary and cardiac, vitamin C, bioflavonoid complex, pantothenic acid, methionine, choline, vitamin B1, vitamin B2, vitamin B6, niacinamide, magnesium, folic acid, organic iodine, vitamin B12, vitamin A, niacin, chromium, rutin, inositol, arnica, proteolytic enzymes, supra oxide dismutase, and tien ma plan. It is preferred that the performance enhancing compositions according to the present invention will be composed entirely of natural substances, while the various raw tissue concentrates will preferably be from bovine or equine sources.

Of the above possible components for the performance enhancing compositions according to the present invention, several components are preferably included in all such compositions, including raw tissue concentrates of adrenal and pituitary, vitamin C, bioflavonoid complex, pantothenic acid, methionine, choline, vitamin B1, vitamin B2, vitamin B6, niacinamide and magnesium. Further, these components will preferably be present in approximately the following relative proportions:

(1)–(5) parts of each of vitamin B1, vitamin B2 and vitamin B6 to
2–10 parts of pituitary raw tissue raw concentrate to
50–100 parts of adrenal raw tissue raw concentrate to
30–80 parts of vitamin C to
8–16 parts of bioflavonoid complex to
10–30 parts of pantothenic acid to
10–20 parts of each of methionine and choline to
8–16 parts of niacinamide to
20–30 parts of magnesium.

The composition is intended to be provided in dosages of approximately 1.0–10.0 mg/lb. animal weight, and it is particularly preferred that the dosage will be 3–4 mg/lb. animal weight.

Several exemplary fluid sample analyses and several corresponding performance enhancing compositions determined on the basis of the analyses are presented below in Tables I–VI. The analysis are set forth in Tables Ia–VIa, while the performance enhancing compositions are set forth in Tables Ib–VIb.

TABLE Ia

| DATE | ANIMAL TYPE | ANIMAL WEIGHT | |
|---|---|---|---|
| | Horse | 1200 lb. | |
| CBC | NORMALS | OPTIMUM | ANALYSIS RESULTS |
| HEMATOLOGY | | | |
| WBC | 5.5–12.5 | 6.5–11.0 | 7.2 |
| RBC | 6.5–12.5 | 7.0–12.0 | 7.11 |
| HGB gm/dl | 11.0–19.0 | 13.0–17.0 | 11.9 |
| HCT % | 32–52 | 32–48 | 33.6 |
| MCV | 34–58 | 40–50 | 47.3 |
| MCH | 12.3–19.7 | 14.0–17.0 | 16.7 |
| MCHC | 31–37 | 32–35 | 35.4 |
| DIFFERENTIAL | | | |
| SEGS | 22–75 | 42–66 | 53.0 |
| LYMPHS | 25–70 | 35–55 | 40.0 |
| MONO | 1–7 | 0–5 | 4.0 |
| BOSIN | 0–11 | <4 | 3.0 |
| BASO | 0–2 | 0–1 | 0 |
| CHEMISTRY - SMAC | | | |
| TRIGLYCERIDE | 30–200 | 70–120 | 31 |
| CHOLESTEROL | 75–150 | 80–110 | 60 |
| ALK PHOS | 80–216 | 80–190 | 175 |
| CALCIUM | 10.0–13.8 | 11–13 | 12.5 |
| PHOSPHORUS | 2.0–5.6 | 3.0–5.0 | 4.5 |
| TOTAL BILI | 0.1–2.0 | same | 1.5 |
| DIRECT BILI | 0.0–0.5 | same | 0.1 |
| INDIRECT BILI | 0.1–2.0 | same | 1.4 |
| TOTAL PROTEIN | 5.7–8.4 | 6.0–7.8 | 6.6 |
| ALBUMIN | 2.3–3.8 | 2.6–3.6 | 3.6 |
| GLOBULIN | 1.6–5.0 | 1.9–4.5 | 3.0 |
| BUN | 10–25 | 10–18 | 19 |
| CREATININE | 1.2–1.9 | 1.3–1.7 | 1.6 |
| URIC ACID | 0.3–1.1 | 0.4–1.0 | 0.2 |
| GLUCOSE | 69–122 | 80–110 | 88 |
| LDH | 142–354 | 150–300 | 192 |
| CPK | 50–350 | 60–300 | 46 |
| SGPT(ALT) | 5–30 | 9–25 | 13 |
| SGOT(AST) | 184–566 | 200–425 | 251 |
| GGT | 3–30 | 8–25 | 32 |
| SODIUM | 130–146 | 130–142 | 140 |
| POTASSIUM | 2.5–5.4 | 3.0–4.8 | 3.9 |
| CO2 | 20–28 | 21–26 | 31 |
| CHLORIDE | 93–109 | 99–106 | 101 |
| ELECT GAP | | | 8 |
| IRON | 40–250 | 50–190 | 161 |

TABLE IIa

| DATE | ANIMAL TYPE | | ANIMAL WEIGHT | |
|---|---|---|---|---|
| | Horse | | 1200 lb. | |
| CBC | NORMALS | OPTIMUM | ANALYSIS RESULTS | |
| HEMATOLOGY | | | | |
| WBC | 5.5–12.5 | 6.5–11.0 | 6.0 | |
| RBC | 6.5–12.5 | 7.0–12.0 | 7.02 | |
| HGB gm/dl | 11.0–19.0 | 13.0–17.0 | 11.1 | |
| HCT % | 32–52 | 32–48 | 30.7 | |
| MCB | 34–58 | 40–50 | 43.7 | |
| MCH | 12.3–19.7 | 14.0–17.0 | 15.8 | |
| MCHC | 31–37 | 32–35 | 36.1 | |
| DIFFERENTIAL | | | | |
| SEGS | 22–75 | 42–66 | 60.0 | |
| LYMPHS | 25–70 | 35–55 | 31.0 | |
| MONO | 1–7 | 0–5 | 7.0 | |
| BOSIN | 0–11 | <4 | 2.0 | |
| BASO | 0–2 | 0–1 | 0 | |
| CHEMISTRY - SMAC | | | | |
| TRIGLYCERIDE | 30–200 | 70–120 | 34 | |
| CHOLESTEROL | 75–150 | 80–110 | 69 | |
| ALK PHOS | 80–216 | 80–190 | 196 | |
| CALCIUM | 10.0–13.8 | 11–13 | 11.8 | |
| PHOSPHORUS | 2.0–5.6 | 3.0–5.0 | 4.3 | |
| TOTAL BILI | 0.1–2.0 | same | 2.1 | |
| DIRECT BILI | 0.0–0.5 | same | 0.1 | |
| INDIRECT BILI | 0.1–2.0 | same | 2.0 | |
| TOTAL PROTEIN | 5.7–8.4 | 6.0–7.8 | 6.0 | |
| ALBUMIN | 2.3–3.8 | 2.6–3.6 | 3.5 | |
| GLOBULIN | 1.6–5.0 | 1.9–4.5 | 2.5 | |
| BUN | 10–25 | 10–18 | 18 | |
| CREATININE | 1.2–1.9 | 1.3–1.7 | 1.5 | |
| URIC ACID | 0.3–1.1 | 0.4–1.0 | 0.0 | |
| GLUCOSE | 69–122 | 80–110 | 97 | |
| LDH | 142–354 | 150–300 | 178 | |
| CPK | 50–350 | 60–300 | 28 | |
| SGPT(ALT) | 5–30 | 9–25 | 14 | |
| SGOT(AST) | 184–566 | 200–425 | 238 | |
| GGT | 3–30 | 8–25 | 56 | |
| SODIUM | 130–146 | 130–142 | 142 | |
| POTASSIUM | 2.5–5.4 | 3.0–4.8 | 3.3 | |
| CO2 | 20–28 | 21–26 | 34 | |
| CHLORIDE | 93–109 | 99–106 | 102 | |
| ELECT GAP | | | 6 | |
| IRON | 40–250 | 50–190 | 134 | |

TABLE IIIa

| DATE | ANIMAL TYPE | | ANIMAL WEIGHT | |
|---|---|---|---|---|
| | Horse | | 1200 lb. | |
| CBC | NORMALS | OPTIMUM | ANALYSIS RESULTS | |
| HEMATOLOGY | | | | |
| WBC | 5.5–12.5 | 6.5–11.0 | 12.0 | |
| RBC | 6.5–12.5 | 7.0–12.0 | 7.28 | |
| HGB gm/dl | 11.0–19.0 | 13.0–17.0 | 13.2 | |
| HCT % | 32–52 | 32–48 | 37.2 | |
| MCV | 34–58 | 40–50 | 51.0 | |
| MCH | 12.3–19.7 | 14.0–17.0 | 18.1 | |
| MCHC | 31–37 | 32–35 | 35.5 | |
| DIFFERENTIAL | | | | |
| SEGS | 22–75 | 42–66 | 78 | |
| LYMPHS | 25–70 | 35–55 | 20.0 | |
| MONO | 1–7 | 0–5 | 1.0 | |
| BOSIN | 0–11 | <4 | 1.0 | |
| BASO | 0–2 | 0–1 | 0 | |
| CHEMISTRY - SMAC | | | | |
| TRIGLYCERIDE | 30–200 | 70–120 | 45 | |
| CHOLESTEROL | 75–150 | 80–110 | 69 | |
| ALK PHOS | 80–216 | 80–190 | 193 | |
| CALCIUM | 10.0–13.8 | 11–13 | 13.0 | |
| PHOSPHORUS | 2.0–5.6 | 3.0–5.0 | 3.1 | |
| TOTAL BILI | 0.1–2.0 | same | 1.9 | |
| DIRECT BILI | 0.0–0.5 | same | 0.1 | |
| INDIRECT BILI | 0.1–2.0 | same | 1.8 | |
| TOTAL PROTEIN | 5.7–8.4 | 6.0–7.8 | 6.9 | |
| ALBUMIN | 2.3–3.8 | 2.6–3.6 | 4.0 | |
| GLOBULIN | 1.6–5.0 | 1.9–4.5 | 2.9 | |
| BUN | 10–25 | 10–18 | 15 | |
| CREATININE | 1.2–1.9 | 1.3–1.7 | 1.3 | |
| URIC ACID | 0.3–1.1 | 0.4–1.0 | 0.1 | |
| GLUCOSE | 69–122 | 80–110 | 81 | |
| LDH | 142–354 | 150–300 | 265 | |
| CPK | 50–350 | 60–300 | 97 | |
| SGPT(ALT) | 5–30 | 9–25 | 17 | |
| SGOT(AST) | 184–566 | 200–425 | 358 | |
| GGT | 3–30 | 8–25 | 24 | |
| SODIUM | 130–146 | 130–142 | 141 | |
| POTASSIUM | 2.5–5.4 | 3.0–4.8 | 3.3 | |
| CO2 | 20–28 | 21–26 | 33 | |
| CHLORIDE | 93–109 | 99–106 | 100 | |
| ELECT GAP | | | 8 | |
| IRON | 40–250 | 50–190 | 182 | |

TABLE IVa

| DATE | ANIMAL TYPE | | ANIMAL WEIGHT | |
|---|---|---|---|---|
| | Horse | | 1200 lb. | |
| CBC | NORMALS | OPTIMUM | ANALYSIS RESULTS | |
| HEMATOLOGY | | | | |
| WBC | 5.5–12.5 | 6.5–11.0 | 8.3 | |
| RBC | 6.5–12.5 | 7.0–12.0 | 8.05 | |
| HGB gm/dl | 11.0–19.0 | 13.0–17.0 | 13.3 | |
| HCT % | 32–52 | 32–48 | 37.9 | |
| MCV | 34–58 | 40–50 | 47.0 | |
| MCH | 12.3–19.7 | 14.0–17.0 | 16.5 | |
| MCHC | 31–37 | 32–35 | 35.1 | |
| DIFFERENTIAL | | | | |
| SEGS | 22–75 | 42–66 | 54.0 | |
| LYMPHS | 25–70 | 35–55 | 38.0 | |
| MONO | 1–7 | 0–5 | 3.0 | |
| BOSIN | 0–11 | <4 | 5.0 | |
| BASO | 0–2 | 0–1 | 0 | |
| CHEMISTRY - SMAC | | | | |
| TRIGLYCERIDE | 30–200 | 70–120 | 26 | |
| CHOLESTEROL | 75–150 | 80–110 | 45 | |
| ALK PHOS | 80–216 | 80–190 | 188 | |
| CALCIUM | 10.0–13.8 | 11–13 | 12.6 | |
| PHOSPHORUS | 2.0–5.6 | 3.0–5.0 | 3.8 | |
| TOTAL BILI | 0.1–2.0 | same | 1.2 | |
| DIRECT BILI | 0.0–0.5 | same | 0.1 | |
| INDIRECT BILI | 0.1–2.0 | same | 1.1 | |
| TOTAL PROTEIN | 5.7–8.4 | 6.0–7.8 | 6.4 | |
| ALBUMIN | 2.3–3.8 | 2.6–3.6 | 3.7 | |
| GLOBULIN | 1.6–5.0 | 1.9–4.5 | 2.7 | |
| BUN | 10–25 | 10–18 | 23 | |
| CREATININE | 1.2–1.9 | 1.3–1.7 | 1.5 | |
| URIC ACID | 0.3–1.1 | 0.4–1.0 | 0.2 | |
| GLUCOSE | 69–122 | 80–110 | 88 | |
| LDH | 142–354 | 150–300 | 244 | |
| CPK | 50–350 | 60–300 | 69 | |
| SGPT(ALT) | 5–30 | 9–25 | 10 | |
| SGOT(AST) | 184–566 | 200–425 | 258 | |
| GGT | 3–30 | 8–25 | 24 | |
| SODIUM | 130–146 | 130–142 | 141 | |
| POTASSIUM | 2.5–5.4 | 3.0–4.8 | 4.0 | |
| CO2 | 20–28 | 21–26 | 32 | |
| CHLORIDE | 93–109 | 99–106 | 101 | |
| ELECT GAP | | | 8 | |
| IRON | 40–250 | 50–190 | 137 | |

TABLE Va

| CBC | NORMALS | OPTIMUM | ANAL 1 | ANAL 2 |
|---|---|---|---|---|
| DATE | | | | |
| ANIMAL TYPE | Horse | | | |
| ANIMAL WEIGHT | | 1200 lb. | | |
| HEMATOLOGY | | | | |
| WBC | 5.5–12.5 | 6.5–11.0 | 10.1 | 7.0 |
| RBC | 6.5–12.5 | 7.0–12.0 | 7.89 | 7.73 |
| HGB gm/dl | 11.0–19.0 | 13.0–17.0 | 13.0 | 13.0 |
| HCT % | 32–52 | 32–48 | 36.5 | 36.7 |
| MCV | 34–58 | 40–50 | 46 | 47.5 |
| MCH | 12.3–19.7 | 14.0–17.0 | 16.5 | 16.9 |
| MCHC | 31–37 | 32–35 | 35.7 | 35.6 |
| DIFFERENTIAL | | | | |
| SEGS | 22–75 | 42–66 | 62 | 54 |
| LYMPHS | 25–70 | 35–55 | 34 | 36 |
| MONO | 1–7 | 0–5 | 0 | 7 |
| BOSIN | 0–11 | <4 | 3 | 3 |
| BASO | 0–2 | 0–1 | 1 | |
| CHEMISTRY - SMAC | | | | |
| TRIGLYCERIDE | 30–200 | 70–120 | | 60 |
| CHOLESTEROL | 75–150 | 80–110 | 69 | 76 |
| ALK PHOS | 80–216 | 80–190 | 151 | 144 |
| CALCIUM | 10.0–13.8 | 11–13 | 12.6 | 13.0 |
| PHOSPHORUS | 2.0–5.6 | 3.0–5.0 | 5.9 | 4.1 |
| TOTAL BILI | 0.1–2.0 | same | 1.5 | 1.4 |
| DIRECT BILI | 0.0–0.5 | same | 0.1 | 0.1 |
| INDIRECT BILI | 0.1–2.0 | same | 1.4 | 1.3 |
| TOTAL PROTEIN | 5.7–8.4 | 6.0–7.8 | 6.0 | 6.4 |
| ALBUMIN | 2.3–3.8 | 2.6–3.6 | 3.8 | 3.6 |
| GLOBULIN | 1.6–5.0 | 1.9–4.5 | 2.2 | 2.8 |
| BUN | 10–25 | 10–18 | 13 | 17 |
| CREATININE | 1.2–1.9 | 1.3–1.7 | 1.2 | 1.5 |
| URIC ACID | 0.3–1.1 | 0.4–1.0 | 0.3 | 0.2 |
| GLUCOSE | 69–122 | 80–110 | 61 | 96 |
| LDH | 142–354 | 150–300 | 213 | 167 |
| CPK | 50–350 | 60–300 | 113 | 79 |
| SGPT(ALT) | 5–30 | 9–25 | 12 | 13 |
| SGOT(AST) | 184–566 | 200–425 | 253 | 251 |
| GGT | 3–30 | 8–25 | 28 | 20 |
| SODIUM | 130–146 | 130–142 | 139 | 143 |
| POTASSIUM | 2.5–5.4 | 3.0–4.8 | 4.3 | 3.9 |
| CO2 | 20–28 | 21–26 | 32 | 33 |
| CHLORIDE | 93–109 | 99–106 | 97 | 101 |
| ELECT GAP | | | | 9 |
| IRON | 40–250 | 50–190 | | 224 |

TABLE VIa

| CBC | NORMALS | OPTIMUM | ANAL 1 | ANAL 2 |
|---|---|---|---|---|
| DATE | | | | |
| ANIMAL TYPE | Horse | | | |
| ANIMAL WEIGHT | | 1200 lb. | | |
| HEMATOLOGY | | | | |
| WBC | 5.5–12.5 | 6.5–11.0 | 9.2 | 8.3 |
| RBC | 6.5–12.5 | 7.0–12.0 | 8.35 | 8.92 |
| HGB gm/dl | 11.0–19.0 | 13.0–17.0 | 14.4 | 15.6 |
| HCT % | 32–52 | 32–48 | 39.9 | 43.7 |
| MCV | 34–58 | 40–50 | 48 | 49 |
| MCH | 12.3–19.7 | 14.0–17.0 | 17.2 | 17.5 |
| MCHC | 31–37 | 32–35 | 36.1 | 35.7 |
| DIFFERENTIAL | | | | |
| SEGS | 22–75 | 42–66 | 57 | 57.0 |
| LYMPHS | 25–70 | 35–55 | 43 | 38.0 |
| MONO | 1–7 | 0–5 | 0 | 5.0 |
| BOSIN | 0–11 | <4 | 0 | 0 |
| BASO | 0–2 | 0–1 | 0 | 0 |
| CHEMISTRY - SMAC | | | | |
| TRIGLYCERIDE | 30–200 | 70–120 | | 59 |
| CHOLESTEROL | 75–150 | 80–110 | 105 | 86 |
| ALK PHOS | 80–216 | 80–190 | 151 | 195 |
| CALCIUM | 10.0–13.8 | 11–13 | 13.7 | 12.3 |
| PHOSPHORUS | 2.0–5.6 | 3.0–5.0 | 4.2 | 3.9 |
| TOTAL BILI | 0.1–2.0 | same | 1.3 | 1.3 |
| DIRECT BILI | 0.0–0.5 | same | 0.1 | 0.1 |
| INDIRECT BILI | 0.1–2.0 | same | 1.2 | 1.2 |
| TOTAL PROTEIN | 5.7–8.4 | 6.0–7.8 | 6.4 | 6.7 |

TABLE VIa-continued

| CBC | NORMALS | OPTIMUM | ANAL 1 | ANAL 2 |
|---|---|---|---|---|
| DATE | | | | |
| ANIMAL TYPE | Horse | | | |
| ANIMAL WEIGHT | | 1200 lb. | | |
| ALBUMIN | 2.3–3.8 | 2.6–3.6 | 4.3 | 4.0 |
| GLOBULIN | 1.6–5.0 | 1.9–4.5 | 2.1 | 2.7 |
| BUN | 10–25 | 10–18 | 12 | 18 |
| CREATININE | 1.2–1.9 | 1.3–1.7 | 1.3 | 1.7 |
| URIC ACID | 0.3–1.1 | 0.4–1.0 | 0.2 | 0.2 |
| GLUCOSE | 69–122 | 80–110 | 75 | 61 |
| LDH | 142–354 | 150–300 | 213 | 226 |
| CPK | 50–350 | 60–300 | 128 | 119 |
| SGPT(ALT) | 5–30 | 9–25 | 15 | 12 |
| SGOT(AST) | 184–566 | 200–425 | 294 | 275 |
| GGT | 3–30 | 8–25 | 17 | 20 |
| SODIUM | 130–146 | 130–142 | 137 | 140 |
| POTASSIUM | 2.5–5.4 | 3.0–4.8 | 4.2 | 4.5 |
| CO2 | 20–28 | 21–26 | 29 | 33 |
| CHLORIDE | 93–109 | 99–106 | 96 | 100 |
| ELECT GAP | | | | 7 |
| IRON | 40–250 | 50–190 | | 217 |

TABLE Ib

| | |
|---|---|
| 660 mg | raw tissue concentrate of Adrenal |
| 36 mg | raw tissue concentrate of Pituitary |
| 525 mg | Vitamin C |
| 135 mg | Bioflavonoid complex |
| 210 mg | Pantothenic acid |
| 180 mg | Methionine |
| 180 mg | Choline |
| 36 mg | Vitamin B1 |
| 36 mg | Vitamin B2 |
| 36 mg | Vitamin B6 |
| 150 mg | Niacinamide |
| 300 mg | Magnesium |
| 500 mg | Vitamin B12 |
| 5 mg | Folic acid |
| 9 mg | Organic iodine |

TABLE IIb

| | |
|---|---|
| 440 mg | raw tissue concentrate of adrenal |
| 24 mg | raw tissue concentrate of Pituitary |
| 144 mg | Vitamin B12 |
| 9600 mcg | Folic acid |
| 350.0 mg | Vitamin C |
| 90 mg | Bioflavonoid complex |
| 140 mg | Pantothenic acid |
| 120 mg | Methionine |
| 120 mg | Choline |
| 24 mg | Vitamin B1 |
| 24 mg | Vitamin B2 |
| 24 mg | Vitamin B6 |
| 100 mg | Niacinamide |
| 200 mg | Magnesium |
| 25.5 mg | Organic iodine |
| 100 mg | Rutin |
| 180 mg | Inositol |

TABLE IIIb

| | |
|---|---|
| 880 mg | raw tissue concentrate of adrenal |
| 48 mg | raw tissue concentrate of Pituitary |
| 1365 mg | Orchic protomorphogen (PMG) |
| 144 mg | Vitamin B12 |
| 9600 mcg | Folic acid |
| 700.0 mg | Vitamin C |
| 180 mg | Bioflavonoid complex |
| 280 mg | Pantothenic acid |
| 240 mg | Methionine |
| 240 mg | Choline |
| 48 mg | Vitamin B1 |
| 48 mg | Vitamin B2 |
| 48 mg | Vitamin B6 |
| 200 mg | Niacinamide |
| 400 mg | Magnesium |

TABLE IIIb-continued

| | |
|---|---|
| 25.5 mg | Organic iodine |

TABLE IVb

| | |
|---|---|
| 880 mg | raw tissue concentrate of adrenal |
| 48 mg | raw tissue concentrate of Pituitary |
| 1365 mg | Orchic protomorphogen (PMG) |
| 72 mg | Vitamin B12 |
| 4800 mcg | Folic acid |
| 700.0 mg | Vitamin C |
| 180 mg | Bioflavonoid complex |
| 280 mg | Pantothenic acid |
| 240 mg | Methionine |
| 240 mg | Choline |
| 48 mg | Vitamin B1 |
| 48 mg | Vitamin B2 |
| 48 mg | Vitamin B6 |
| 200 mg | Niacinamide |
| 400 mg | Magnesium |
| 3000 IU | Vitamin A |
| 57 mg | Niacin |
| 288 mcg | Chromium |
| 25.5 mg | Organic iodine |

TABLE Vb

| | |
|---|---|
| 660 mg | raw tissue concentrate of adrenal |
| 36 mg | raw tissue concentrate of Pituitary |
| 1365 mg | Orchic protomophogen (PMG) |
| 72 mg | Vitamin B12 |
| 4800 mcg | Folic acid |
| 525.0 mg | Vitamin C |
| 135 mg | Bioflavonoid complex |
| 210 mg | Pantothenic acid |
| 180 mg | Methionine |
| 180 mg | Choline |
| 36 mg | Vitamin B1 |
| 36 mg | Vitamin B2 |
| 36 mg | Vitamin B6 |
| 150 mg | Niacinamide |
| 300 mg | Magnesium |

TABLE Ib

| | |
|---|---|
| 880 mg | raw tissue concentrate of adrenal |
| 48 mg | raw tissue concentrate of Pituitary |
| 1170 mg | Orchic protomorphogen |
| 36 mg | Vitamin B12 |
| 2400 mcg | Folic acid |
| 270 mg | Thyroid PMG extract |
| 709.6 mg | Vitamin C |
| 180 mg | Bioflavonoid complex |
| 280 mg | Pantothenic acid |
| 240 mg | Methionine |
| 240 mg | Choline |
| 48 mg | Vitamin B1 |
| 48 mg | Vitamin B2 |
| 48 mg | Vitamin B6 |
| 200 mg | Niacinamide |
| 400 mg | Magnesium |
| 3000 IU | Vitamin A |
| 57 mg | Niacin |
| 288 mcg | Chromium |

Referring to Table Ia, it will be noted that the analysis results set forth therein correspond to the analysis of an initial blood sample drawn from a horse weighing approximately 1200 lbs., and that the information set forth under the Normals and Optimum columns is the predetermined, appropriate compositional parameters against which the analysis results are compared. Referring to Table Ib, the performance enhancing composition set forth therein is determined, as discussed above, on the basis of: (1) a comparison of the analysis results to the predetermined appropriate parameters, which indicated that the HGB (Hemoglobin), triglyceride, cholesterol, uric acid, and CKP (creatine phosphokinase) components were below optimal levels and that the MCHC (mean corpuscular hemoglobin concentrate), BUN (blood urea nitrogen), GGT (gamma-glutamyl transpeptidase) and $CO_2$ (carbon dioxide) components were above optimal levels; and (b) on additional predetermined data, which primarily includes experimental data indicating possible substances which could be administered to the horse (or other animal in question) for overcoming the specifically detected deficiencies and excesses in the analyzed composition of the animal's blood.

Tables IIa-IVa and Tables IIb-IVb are substantially similar to tables Ia and Ib, respectively, although the analysis results and the corresponding performance enhancing composition are distinct from those set forth in Tables Ia, Ib. Tables Va-VIa are slightly different from Table Ia in that two samples of a horse's blood have been obtained and analyzed. The analysis results of the first sample correspond to an initial blood sample such as analyzed in relation to Table Ia, while the second column of analysis results pertain to a blood sample which was drawn approximately one month after the first sample had been drawn and after a performance enhancing composition (which has been determined on the basis of the initial sample analysis) had been administered to the animal during the time period between drawing of the first and second fluid samples. The performance enhancing compositions set forth in Tables Vb-IVb are modified compositions such as determined in step $P_{10}$, and are determined on the basis of the second or later fluid sample analysis set forth in Tables Va and VIa, respectively.

Note that the specific performance enhancing compositions as set forth in Tables Ib-VIb are indicated as specific quantities of each of the components in a single dosage of the composition to be administered to the animal. As discussed above, such dosage is preferably orally administered to the animal on a bi-daily basis prior to feeding, and for a predetermined time period generally within the range of 30-60 days.

According to another preferred embodiment of the present invention, a composition for use in improving an animal's performance comprises adrenal and pituitary raw tissue concentrates, vitamin C, bioflavonoid complex, pantothenic acid, methionine, choline, vitamin B1, vitamin B2, vitamin B6, niacinamide, magnesium, vitamin B12, folic acid and organic iodine. Again it is preferred that this composition will be composed entirely of natural substances, that the adrenal and pituitary raw tissue concentrates will be obtained from bovine or equine sources, and that the composition is provided in powder or liquid form so that it can be orally administered to an animal. This composition has been specifically developed for enhancing the performance of racing horses and has been found to be most effective if orally administered to the animal in solution form 3-5 hours prior to the animal's performance. It is also preferred that relative proportions of the components in the composition will be:
- at least 40 parts adrenal raw tissue concentrate to
- at least 2 parts pituitary raw tissue concentrate to
- 30-60 parts vitamin C to
- 20-30 parts magnesium to
- 10-20 parts of each of pantothenic acid, methionine and choline to
- 8-15 parts of each of niacinamide and bioflavonoid complex to 1-5 parts of each of vitamins B1, B2 and B6 to
0.1-1 parts organic iodine to
0.05-0.5 parts folic acid.

It is particularly preferred that the relative proportions of the components will be approximately:
at least 48 parts adrenal raw tissue concentrate to
at least 2.8 parts pituitary raw tissue concentrate to
42-48 parts vitamin C to
23-24 parts magnesium to
16-18 parts pantothenic acid to
13-15 parts of each of methionine and choline to
11-13 parts niacinamide to
10-11 parts bioflavonoid complex to
2-3 parts of each of vitamins B1, B2 and B6 to
0.3-0.5 parts organic iodine to
0.1-0.2 parts folic acid.

The composition is intended to be provided in dosages of approximately 1.0-10.0 mg/lb. of animal weight, and it is particularly preferred that the dosage will be approximately 3-4 mg/lb. of animal weight.

Although there have been described what are at present considered to be the preferred embodiments of the invention, it will be understood that various modifications will be made therein without departing from the spirit or essential characteristics thereof. The present embodiments are therefore to be considered in all aspects as illustrative and not restrictive. The scope of the invention is indicated by the appended claims rather than by the foregoing description.

I claim:

1. A composition for use in improving an animal's performance, comprising:
    adrenal and pituitary raw tissue concentrates, vitamin C, bioflavonoid complex, pantothenic acid, methionine, choline, vitamin B1, vitamin B2, vitamin B6, niacinamide and magnesium; and
    said composition is composed entirely of natural substances.

2. A composition according to claim 1, wherein:
    relative proportions of said components are approximately:
    1-6 parts of each of vitamin B1, vitamin B2 and vitamin B6 to
    2-10 parts of pituitary raw tissue concentrate
    40-100 parts of adrenal raw tissue concentrate to
    30-80 parts of vitamin C to
    8-16 parts of bioflavonoid complex to
    10-30 parts of pantothenic acid to
    10-20 parts of each of methionine and choline to
    8-16 parts of niacinamide to
    20-30 parts of magnesium.

3. A composition according to claim 1, further comprising one or more of:
    concentrates of thyroid, orchic protomorphogen, thymus, spleen, kidney, hypothalamus, pulmonary and cardiac, folic acid, iodine, vitamin B12, vitamin A, niacin, chromium, rutin, inositol, arnica, proteolytic enzymes, supra oxide dismutase and tien ma plan in varying relative proportions based on an analysis of a fluid sample of a specific animal to which the composition is to be administered.

4. A composition according to claim 1, wherein said composition is adapted to be orally administered to an animal on a bi-daily basis.

5. A composition according to claim 1, wherein said composition is provided in dosages of approximately 1.0-6.0 mg/lb of animal weight.

6. A composition for use in improving an animal's performance, comprising:
    adrenal and pituitary raw tissue concentrates, vitamin C, bioflavonoid complex, pantothenic acid, methionine, choline, vitamin B1, vitamin B2, vitamin B6, niacinamide, magnesium, vitamin B12, folic acid and iodine.

7. A composition according to claim 6, wherein relative proportions of said components are approximately:
    at least 48 parts of adrenal raw tissue concentrate to
    at least 2.8 parts pituitary raw tissue concentrate to
    42-48 parts of vitamin C to
    23-24 parts magnesium to
    16-18 parts pantothenic acid to
    13-15 parts methionine to
    13-15 parts choline to
    11-13 parts niacinamide to
    10-11 parts bioflavonoid complex to
    2-3 parts of each of vitamins B1, B2 and B6 to
    0.3-0.5 parts organic iodine to
    0.1-0.2 parts folic acid.

8. A composition according to claim 6, wherein said composition is composed entirely of natural substances.

9. A composition according to claim 6, wherein said composition is adapted to be orally administered to an animal 3-5 hours prior to a performance of the animal.

10. A composition according to claim 9, wherein said composition is provided in dosages of approximately 1.0-10.0 mg/lb. of animal weight.

11. A composition according to claim 6, wherein relative proportions of said components are approximately:
    at least 40 parts adrenal raw tissue concentrate to
    at least 2 parts pituitary raw tissue concentrate to
    30-60 parts vitamin C to
    20-30 parts magnesium to
    10-20 parts of each of pantothenic acid, methionine and choline to
    8-15 parts of each of niacinamide and bioflavonoid complex to
    1-5 parts of each of vitamins B1, B2 and B6 to
    0.1-1 parts iodine to
    0.05-0.5 parts folic acid.

12. A method of biochemically enhancing an animal's performance, comprising the steps of:
    (a) obtaining a sample of a body fluid of an animal which is performing below expected levels;
    (b) analyzing said sample to determine a composition thereof;
    (c) comparing said determined composition of said fluid to predetermined appropriate parameters;
    (d) determining a performance enhancing composition to be administered to said animal based on said comparison and on additional predetermined data;
    said performance enhancing composition comprising adrenal raw tissue concentrate, pituitary raw tissue concentrate, vitamin C, bioflavonoid complex, pantothenic acid, methionine, choline, vitamin B1, vitamin B2, vitamin B6, niacinamide and magnesium;
    (e) administering a predetermining dosage of said performance enhancing composition to said animal for a predetermined time period; and
    (f) repeating steps (a)-(c) to determine if a desired change in said fluid composition of said animal has been achieved.

13. A method according to claim 12, wherein said body fluid is blood.

14. A method according to claim 13, wherein chemical, hematological and differential components of said fluid are analyzed in said step (b).

15. A method according to claim 12, wherein said dosage of said performance enhancing composition is orally administered to said animal twice daily for at least one week in step (e).

16. A method according to claim 12, wherein relative proportions of said components in said performance enhancing composition are approximately:
- 3 parts of each of pituitary raw tissue concentrate, vitamin B1, vitamin B2, and vitamin B6 to
- 53 parts of adrenal raw tissue concentrate to
- 42 parts of vitamin C to
- 11 parts of bioflavonoid complex to
- 17 parts of pantothenic acid to
- 14.5 parts of each of methionine and choline to
- 12 parts of niacinamide to
- 24 parts of magnesium.

17. A method according to claim 12, wherein said performance enhancing composition further comprises at least one of concentrates of thyroid, orchic protomorphogen, thymus, spleen, kidney, hypothalamus, pulmonary and cardiac, folic acid, organic iodine, niacin, chromium, vitamin B12, vitamin A, rutin, inositol, arnica, proteolytic enzymes, supra oxide dismutase and tien ma plan.

18. A method according to claim 12, wherein said performance enhancing composition is composed entirely of natural substances.

19. A method according to claim 12, including a further step of:
  (g) administering a progressively smaller quantity of said performance enhancing composition to said animal for an additional predetermined period of time after a desired change in the composition of a fluid sample of the animal has been achieved.

20. A method according to claim 12, wherein said dosage of said performance enhancing composition is orally administered to said animal twice daily for a period of 30–60 days in step (e).

* * * * *